US008765399B2

(12) United States Patent
Riska

(10) Patent No.: US 8,765,399 B2
(45) Date of Patent: Jul. 1, 2014

(54) **CULTURES AND PROTOCOLS FOR DIAGNOSIS OF TOXIGENIC *CLOSTRIDIUM DIFFICILE***

(75) Inventor: Paul Riska, New York, NY (US)

(73) Assignee: Montefiore Medical Center, Bronx, NY (US)

( * ) Notice: Subject to any disclaimer, the term of this patent is extended or adjusted under 35 U.S.C. 154(b) by 271 days.

(21) Appl. No.: 13/068,682

(22) Filed: May 17, 2011

(65) Prior Publication Data

US 2011/0287474 A1   Nov. 24, 2011

Related U.S. Application Data

(60) Provisional application No. 61/395,807, filed on May 18, 2010.

(51) Int. Cl.
  *C12N 1/20*  (2006.01)
  *C12Q 1/04*  (2006.01)
  *C12N 1/00*  (2006.01)
  *C12Q 1/00*  (2006.01)
  *C12Q 1/02*  (2006.01)

(52) U.S. Cl.
  USPC ............. 435/34; 435/252.7; 435/29; 435/4; 435/244; 435/252.1

(58) Field of Classification Search
  None
  See application file for complete search history.

(56) References Cited

U.S. PATENT DOCUMENTS

| | | | |
|---|---|---|---|
| 4,530,833 | A | 7/1985 | Wilkins et al. |
| 4,533,630 | A | 8/1985 | Wilkins et al. |
| 4,863,852 | A | 9/1989 | Wilkins et al. |
| 4,879,218 | A | 11/1989 | Wilkins et al. |
| 5,098,826 | A | 3/1992 | Wilkins et al. |
| 5,965,375 | A | 10/1999 | Valkirs |
| 6,503,722 | B1 | 1/2003 | Valkirs |
| 7,179,611 | B2 | 2/2007 | Deutsch |

OTHER PUBLICATIONS

Laughon, Barbara E.; et al; "Enzyme Immunoassays for Detection of *Clostridium difficile* Toxins A and B in Fecal Specimens." The Journal of Infectious Diseases, 149, 781-788, 1984.*
Paredes-Sabja, Daniel; et al; "Germination of spores of *Clostridium difficile* strains, including isolates from a hospital outbreak of *Clostridium difficile*-associated disease." Microbiology, 154, 2241-2250, 2008.*
Borriello, Saverio P.; et al; "Simplified procedure for the routine isolation of *Colstridium difficile* from faeces." Journal of Clinical Pathology, 34, 1124-1127, 1981.*
Jump, Robin L.P.; et al; "Vegetative *Clostridium dfficile* Survives Room Air on Moist Surfaces and in Gastric Contents with Reduced Acidity: a Potential Mechanism to Explain the Association Between Proton Pump Inhibitors and *C. difficile*-Associated Disease?" Antimicrobial Agents and Chemotherapy, 51, 2883-2887, 2007.*
Arce J et al., Potential Impact of Two-Stage *Clostridium difficile* ELISA testing on Clinical Decision Making. Abstract, Society for Microbiology Meeting, Philadelphia PA, May 17-21, 2009.
Tyrrell KL et al., Evaluation of CCFA and CCFA-HT agars and CCMB-TAL broth for recovery of *Clostridium difficile* from fecal samples. Abstract, Society for Microbiology Meeting, Philadelphia PA, May 17-21, 2009.
Kvach E J et al., entitled "Comparison of BD GeneOhm Cdiff Real-Time PCR Assay with a Two-Step Algorithm and a Toxin A/B Enzyme-Linked Immunosorbent Assay for Diagnosis of Toxigenic *Clostridium difficile* Infection," Journal of Clinical Microbiology, vol. 48, No. 1, Jan. 2010, p. 109-114; Epub Oct. 28, 2009.
Arce J et al., Potential Impact of Two-Stage *Clostridium difficile* ELISA testing on Clinical Decision Making. Poster presented at American Society for Microbiology, Philadelphia PA, May 19, 2009.
Kim KB et al., Selective enrichment broth culture increased the toxigenic *Clostridium difficile* detection rate of a dual antigen and toxin A/B EIA assay by 54.5%. Abstract American Society for Microbiology meeting, May 2010.
Sharp SE et al., Evaluation of the C.Diff Quik Chek Complete Assay, a new glutamate dehydrogenase and A/B toxin combination lateral flow assay for use in rapid, simple diagnosis of *clostridium difficile* disease. J Clin Microbiol. Jun. 2010;48(6):2082-6. Epub Apr. 7, 2010.
Perry JD et al., Evaluation of a chromogenic culture medium for isolation of *Clostridium difficile* within 24 hours. J Clin Microbiol. Nov 2010;48(11):3852-8. Epub Aug. 25, 2010.
Tyrrell KL et al. Evaluation of CCFA and CCFA-HT agars and CCMB-TAL broth for recovery of *Clostridium difficile* from fecal samples, poster, Am Soc Microbiol Meeting, May 19, 2009.
Clabots C et al. "Detection of asymptomatic *Clostridium difficile* carriage by an alcohol shock procedure." Journal of Clinical Microbiology, (1989) 27(10): 2386-2387.
Eckert C et al. "Evaluation of the chromogenic agar chromID *C. difficile*." Journal of Clinical Microbiology (2003) 51: 1002-1004.
Sharp S et al. "A simple 3-step algorithm for improved laboratory detection of *Clostridium difficile* toxin without the need for tissue culture cytotoxicity neutralization assays." Diagnostic Microbiology and Infectious Disease 64 (2009) p. 344-346.
She R et al. "Evaluation of enzyme immunoassays to detect *Clostridium difficile* toxin from anaerobic stool culture." Am. J. Clin. Pathol. 2009, 131:81-84.

* cited by examiner

*Primary Examiner* — Blaine Lankford
*Assistant Examiner* — David Berke-Schlessel
(74) *Attorney, Agent, or Firm* — Amster, Rothstein & Ebenstein LLP

(57) ABSTRACT

Disclosed are culture media, protocols and kits for diagnosis of toxigenic *Clostridium difficile*, where the culture medium comprises Cooked Meat Medium with glucose; yeast extract; taurocholate; cycloserine; and cefoxitin.

33 Claims, 2 Drawing Sheets

CULTURES AND PROTOCOLS FOR DIAGNOSIS OF TOXIGENIC CLOSTRIDIUM DIFFICILE

CROSS-REFERENCE TO RELATED APPLICATION

This application claims the benefit of U.S. Provisional Patent Application No. 61/395,807, filed May 18, 2010, the content of which is incorporated by reference.

FIELD OF THE INVENTION

The present invention relates generally to cultures and protocols for diagnosis of toxigenic Clostridium difficile.

BACKGROUND OF THE INVENTION

Throughout this application various publications are referred to in short form. Full citations for these references may be found at the end of the specification. The disclosures of these publications are hereby incorporated by reference in their entirety into the subject application to more fully describe the art to which the subject invention pertains.

Clostridium difficile, an anaerobic spore-forming bacterium, was found in the 1970s to be the cause of pseudomembranous colitis, and the major agent of antibiotic-associated diarrhea, causing about 20% of cases (Dubberke et al. 2009, Kelly, 2008). The diarrheal disease is due to expression of major toxins A and B by "toxigenic" C. difficile strains; other strains of this bacterium do not contain the genes for these toxins and are entirely non-pathogenic (Kelly, 2008). Infectious spores of C. difficile can survive in the environment for months, resist drying and many common disinfectants, and thus represent a major reservoir of this organism within hospitals (Dubberke et al. 2009). With the arrival of a new "hypervirulent" strain in the past decade, the incidence of C. difficile disease and its severity have increased dramatically (Kelly 2008, Dubberke et al. 2009). C. difficile is now the leading hospital-acquired infection in some regions of North America, affecting over 1 out of 100 hospitalized adults (APIC, 2008, Jarvis et al., 2009). There were an estimated 300,000 infections in acute care hospitals in the US annually in 2005 (Dubberke et al. 2009) and an equal number in long-term care facilities (Ohio DOH, 2007). While in the past these infections were merely a nuisance, the new C. difficile now has an attributable mortality of ~7%, and contributes to death in another 7.5% of patients (Kelly 2008). A further problem is that current treatments are plagued by a 20-50% recurrence rate, with many patients continuing to relapse with this condition for years (Kelly 2008, Dubberke et al. 2009). The overall costs of C. difficile disease are estimated to be as high as $3.2 billion annually (Dubberke et al. 2009, Cohen et al. 2010).

Diagnosis of C. difficile: Clostridium difficile disease was initially identified by anaerobically growing the organism on selective culture media (George et al. 1979; Buggy et al. 1983)), which required 2 days and failed to distinguish between toxigenic and nontoxigenic strains. The presence of toxins needed to be confirmed from culture; this involved a 48 hr cytotoxicity assay using tissue cultured epithelial cells; specificity of cytotoxicity was demonstrated by its neutralization by Clostridia-specific anti-toxin. Alternatively, cytotoxicity could be detected directly in preparations of stool samples (George et al. 1979). However, due to the labor-intensive and technically complex nature of this assay, it was quickly replaced in the 1990s by Enzyme-linked Immunosorbent Assays (EIAs or ELISAs) directed at the toxin A, or later toxin A & B antigens (Planche et al. 2008, Cohen et al. 2010). While in experimental settings, these assays had sensitivities reported to be over 90%, recent evidence shows that in day-to-day practice, their sensitivity was reduced to below 50% (Ticehurst et al. 2006, Reller et al. 2007, Fenner et al. 2008, Sloan et al. 2008, Stamper et al. 2009). Why this discrepancy occurs is not clear, though it may relate to the lability of C. difficile toxins in clinical samples, or possibly changes in antibody affinity for their epitopes. Failure to detect C. difficile, in the current epidemic is no longer acceptable, so alternative strategies for diagnosis are needed.

One approach involves identifying samples that contain C. difficile by using an EIA for an abundant, stable antigen, the glutatamate dehydrogenase (gdh) protein (Ticehurst et al. 2006, Fenner et al. 2008, Gilligan 2008). This test is rapid, much more sensitive than toxin A/B EIA, but fails to discriminate toxigenic from non-toxigenic strains. Thus, while its useful in eliminating patients without C. difficile (due to a high negative predictive value) (Reller et al. 2007, Kvach et al. 2010), its positive predictive value is low—about ⅓ of those positive by gdh EIA do not have toxigenic strains. Thus, those patients found to have a positive gdh EIA need to be assessed by alternate means, which could be an insensitive toxin EIA or the traditional 48 hr cytotoxicity tissue culture assay Another approach for detecting toxigenic C. difficile involves amplification of the toxin B gene by polymerase chain reaction (PCR). Commercial reagents for PCR directly from stool have been FDA-approved from several manufacturers in the past year, and these assays are rapid, sensitive and specific (Stamper et al. 2009, Kvach et al. 2010). However, they are costly (up to 10 times the cost of the EIA test), and require some technical expertise.

Finally, toxigenic culture remains the gold standard by which most diagnostic assays are judged, as acknowledged by recent national guidelines (Cohen, 2010). It has not been widely adapted due to i) the delay in getting results (2 to 7 days) and ii) the technical expertise and equipment required (often including an anaerobic chamber). Nonetheless, various modifications of toxigenic culture have consistently demonstrated the highest accuracy in detecting C. difficile infection. While most reported studies have focused on solid agar cultures, which allow colony morphology to guide identification, there have been several reports of liquid culture used for diagnosis. In the 1980s, chopped meat broth was utilized to maintain anaerobiosis, and accurate detection of C. difficile was reported within 24-48 hrs using gas liquid chromatography to detect the volatile amines characteristic of this organism (Buchanan 1984, Johnson et al. 1989). 225 of 226 strains were detected by this method; however, these included non-toxigenic strains (Johnson et al. 1989).

A modification of the basic CCFA agar was used to create a broth, but its performance was no better than the agar (Clabots et al. 1991). Recently, a re-examination of this broth, with incorporation of the bile salt taurocholate to promote germination of spores (Buggy et al. 1983), showed its utility for clinical and environmental isolates (Arroyo et al. 2005, Neranzdic et al. 2009). A commercial form of this broth exists (Anaerobe Systems AS-8216, Morgan Hill, Calif.), but it requires an anaerobic environment for culture, limiting its general applicability. Again, most forms of culture require confirmation of cytotoxin production, which has been usually done using the 48 hr cytotoxicity assay.

The present invention addresses the need for improved methods for diagnosis of toxigenic *C. difficile*.

SUMMARY OF THE INVENTION

The present invention provides culture media for *Clostridium difficile* comprising Cooked Meat Medium with glucose; yeast extract; taurocholate; cycloserine; and cefoxitin.

The invention also provides methods for diagnosing the presence of toxigenic *Clostridium difficile* in a sample, comprising: a) treating the sample with alcohol; b) incubating the alcohol-treated sample in a medium comprising Cooked Meat Medium with glucose; yeast extract; taurocholate; cycloserine; and cefoxitin for 24-72 hrs; and c) testing the sample after the 24-72 hour incubation of step b) for the presence of *C. difficile* toxin A and/or toxin B; wherein the presence of *C. difficile* toxin A and/or toxin B indicates the presence of *Clostridium difficile* in the sample.

The invention further provides kits for diagnosing the presence of toxigenic *Clostridium difficile* comprising culture media and protocols disclosed herein.

DETAILED DESCRIPTION OF THE INVENTION

Figure 1:
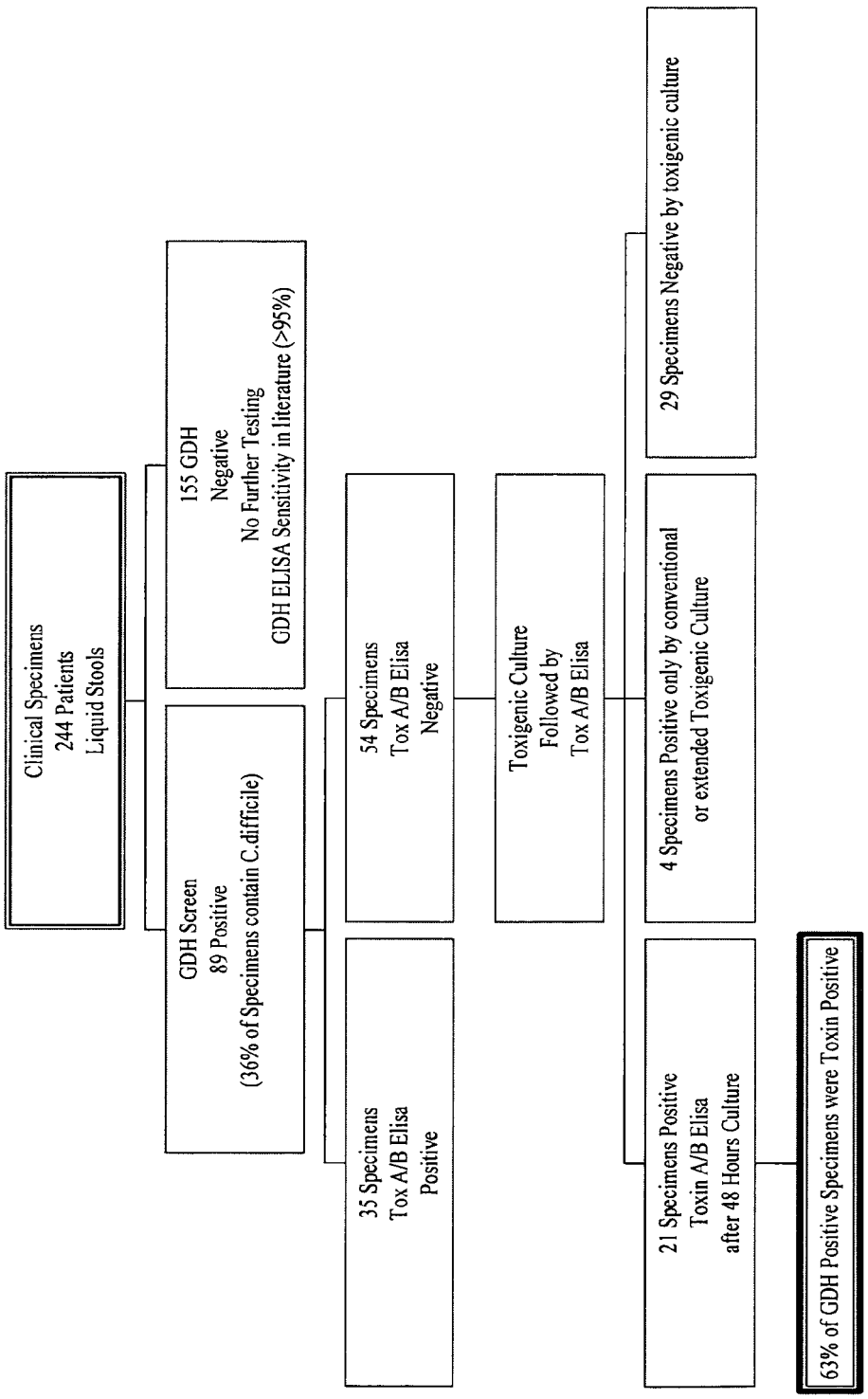
FIG. 1. Summation of validation study for two-step toxin protocol.

The present invention provides a culture medium for *Clostridium difficile* comprising Cooked Meat Medium with glucose; yeast extract; taurocholate; cycloserine; and cefoxitin. Optionally, the culture medium also includes Hemin and/or Vitamin K. In one embodiment, the culture medium consists essentially of the indicated components. Preferably, taurocholate is present in a concentration of 0.05-0.1%, or more preferably 1.0 mg/mL. Preferably, cycloserine is present in a concentration of 200 to 400 µg/ml, or more preferably 250 µg/ml. Preferably, cefoxitin is present in a concentration of 8 to 32 µg/ml, or more preferably 16 µg/ml. Preferably, yeast extract is present in a concentration of 2 to 10 gm/liter, or more preferably about 5 gm/liter.

The invention also provides a method for diagnosing the presence of toxigenic *Clostridium difficile* in a sample, comprising:

a) treating the sample with alcohol;

b) incubating the alcohol-treated sample in a medium comprising Cooked Meat Medium with glucose; yeast extract; taurocholate; cycloserine; and cefoxitin for 24-72 hrs; and c) testing the sample after the 24-72 hour incubation of step b) for the presence of *C. difficile* toxin A and/or toxin B;

wherein the presence of *C. difficile* toxin A and/or toxin B indicates the presence of *Clostridium difficile* in the sample.

The sample can be, for example, a stool sample or an environmental sample. Environmental samples can be obtained from, for example, surfaces suspected of being contaminated with *Clostridium difficile*, such as, for example, hospital equipment.

The alcohol used in the method can be, for example, methanol, ethanol or propanol, and is preferably ethanol. Preferably, the ratio of sample to alcohol in step a) is 50-500 µl of sample to 1 ml of alcohol. More preferably, the ratio of sample to alcohol in step a) is about 200 µl of sample to 1 ml of alcohol. Preferably, the final concentration of ethanol after addition of the sample in step a) is 50-90% ethanol.

Preferably, for step a), the duration of treatment ranges from 15 minutes to 1 month, and more preferably the duration of treatment is 30 minutes.

Preferably, in step b), the ratio of alcohol treated sample to Cooked Meat Medium is 50-250 µl of alcohol treated sample to 10 ml of Cooked Meat Medium.

The medium in step b) can also include Hemin and/or Vitamin K. In one embodiment, the medium consists essentially of the indicated components. Preferably, taurocholate is present in a concentration of 0.05-0.1%, or more preferably 1.0 mg/mL. Preferably, cycloserine is present in a concentration of 200 to 400 µg/ml, or more preferably 250 µg/ml. Preferably, cefoxitin is present in a concentration of 8 to 32 µg/ml, or more preferably 16 µg/ml. Preferably, yeast extract is present in a concentration of 2 to 10 gm/liter, or more preferably about 5 gm/liter.

Preferably, step b) is carried out at a temperature of 37° C. Preferably, step b) is carried out for 48 hours.

Methods for detecting the presence of *C. difficile* toxin A and toxin B have been described (e.g., U.S. Pat. Nos. 4,530,833, 4,533,630, 4,863,852, 4,879,218, 5,098,826, 5,965,375, 6,503,722 and 7,179,611). Preferably, the presence of *C. difficile* toxin A and/or toxin B can be tested using an EIA assay, such as, for example, Meridien Biosciences Premier Toxin A/B kit (Cincinnati, Ohio) or *C. DIFFICILE* TOX A/B II (TechLab, Blacksburg, Va.).

The invention also provides a kit for diagnosing the presence of toxigenic *Clostridium difficile* where the kit comprises any of the culture media disclosed herein. The kit can also include alcohol, such as for example ethanol. The kit can also include instructions for carrying out any of the methods disclosed herein.

EXPERIMENTAL DETAILS

The present invention includes a protocol for performing *C. difficile* toxigenic culture from samples, such as stool samples, in 48 hrs. The protocol includes 4 components:

1. restriction of competing microflora by use of alcohol such as ethanol shock to kill all vegetative bacteria in the stool sample, and the addition of cycloserine and cefoxitin to the broth to inhibit growth of competing Clostridia and other spore-bearing species;
2. use of chopped meat broth, also known as cooked meat broth (CMB), which provides an anaerobic environment and allows growth of *C. difficile* without requiring an anaerobic chamber;
3. addition of taurocholate to the broth to facilitate rapid germination of spores and brisk toxin A/B production; and
4. use of a rapid (~1 hr) toxin A/B EIA assay directly from a 48 hr broth culture to detect toxigenic strains.

The rationale for each step is as follows.

It is unlikely that vegetative (non-sporulated, dividing) cells of *C. difficile* survive for more than 15 minutes within an aerobic environment (Arroyo et al. 2005), so that most culture assays for viable *C. difficile* are detecting spores within a clinical sample. *C. difficile* spores are quite stable in ethanol, surviving for up to 1 month in suspension in 70% ethanol at 4° C., without declining titer (unpublished data). Thus, there is no harm to treating stool samples with ethanol to suppress background microflora, and to help homogenize the specimen. However, data show that any concentration of ethanol above 5% will impair growth of vegetative cells in CMB (unpublished data), so care must be taken to ensure that no more than 250 μl of ethanol slurry is added to a 10 ml culture tube.

The most stable anaerobic environment for growing *C. difficile* outside an anaerobic chamber is provided by chopped meat broth. Homogeneous broths based on brain-heart infusion (BHI) and incorporating thioglycollate or cysteine as reducing agents failed to consistently support growth of clinical strains of *C. difficile*, unless they were used within 1 hr of autoclaving. In contrast, Hemin, Vitamin K and glucose supplemented CMB (Becton Dickinson #297809 or Anaerobe Systems AS-811) consistently supported growth of *C. difficile*. Meanwhile, unsupplemented CMB from BD (#221508) failed to allow growth of *C. difficile*—the key missing component was not Vitamin K or glucose but yeast extract.

The addition of cycloserine and cefoxitin to the CMB inhibits growth of most other Clostridia, which could also survive the ethanol shock process and might outcompete *C. difficile* for growth. Preliminary work shows that, similar to George et al. (1983), 6 clinical strains of *C. difficile* can grow in broth despite concentrations of cefoxitin and cycloserine at 6× the dose used in CCFA (500 µg/ml of cycloserine and 16 µg/ml cefoxitin). Surprisingly, a CDC reference strain of the NAP1 epidemic type was inhibited in CMB with 500 µg/ml, but not 250 µg/ml of cycloserine, necessitating the use of the lower cycloserine concentration. Levett (1984) and Clabots (1991) had shown similar results when using CCFA plates.

Taurocholate has been known to facilitate germination/growth of *C. difficile* spores (Buggy et al. 1983). As toxin production primarily occurs in stationary phase (Kelly et al. 2008), which occurs after a period of abundant growth, it is expected that the more rapidly growth occurs, the more toxin is produced—both from the larger numbers of bacteria as well as their entry into stationary phase growth. The epidemic strain is notable for producing toxins even during its actively-growing stage, and has been shown to produce greater than 10-fold more toxin in vitro (Kelly et al. 2008), so that it should be easier to detect with a toxin assay.

Toxin A/B EIA applied to turbid CMB broths, 48 hrs after inoculation as above, reliably detected the presence of toxigenic *C. difficile*, which was confirmed by other means (PCR, plating on CCFA) as shown below. The homogenized supernatant of the CMB broth is a far more reliable testing substrate than a stool sample. In contrast, toxin EIA applied to colonies on an agar plate has not been shown to be highly reproducible (She, 2009), perhaps because toxin is secreted by bacterial cells into their milieu, and thus may diffuse into the agar rather than staying attached to the bacterial cells forming a colony.

Full Protocol:
Materials:
1. *C. difficile* selective Chopped Meat Broth (CMB-S) was prepared by adding the following compounds to Cooked Meat Medium with Glucose, Hemin & Vitamin K (BD, Cockeysville, Md.): taurocholate (1.0 mg/mL), cycloserine (250 µg/mL) and cefoxitin (16 µg/mL) (all Sigma Chemical, St. Louis, Mo.). These were stored at 4° C. and used within 1 month. Each batch was quality-controlled by allowing growth of the CDC 2005-005 reference NAP1 strain. Cooked Meat Medium is described, for example in Robertson (1916).
2. Meridien Biosciences Premier Toxin A/B kit (Cincinnati, Ohio) or *C. DIFFICILE* TOX A/B II (TechLab, Blacksburg, Va.)
3. C. DIFF QUIK CHEK®-60-TechLab (Blacksburg, Va.)
4. Ethanol.
Effective range of reagents used: cycloserine 200 to 400 µg/ml, cefoxitin 8 to 32 µg/ml, taurocholate (0.05-0.1%), and ethanol 50-90% (final concentration after addition of sample).

Methods:
1. Stool samples are used fresh within 24 hrs, or frozen at −20° C. up to 1 week. When thawed, ~200 µl of stool specimen is added to 1 ml of 100% ethanol in a 5 ml snap-top tube.
2. Slurry is vortexed for 10 sec to disperse and held at room temp for 30 minutes.
3. 100 µl of the treated stool is inoculated with a Pasteur pipette (sterile) into CMB-S.
4. CMB-S is incubated for 48 hrs at 37° C.
5. If there is visible growth in broth after 48 hrs, then it is vortexed briefly, allowing large clumps of meat to settle (~1 min).
6. CMB-S broth is tested for toxins A/B by EIA (Meridien Premier or *C. DIFFICILE* TOX A/B II), using 100 ul of vortexed supernatant instead of stool, then following the kit protocol.

Samples to be tested may be pre-screened by using a gdh EIA such as C. DIFF QUIK CHEK®-60, whereby only gdh-positive samples would be tested further. Alternatively, specimens can be tested without any pre-selection.

Results

In the first study incorporating the above protocol, 244 samples were tested by gdh EIA assay (Techlab, Blacksburg, Va.), and those positive (n=89) were then tested by toxin A/B EIA (Meridien). Those samples with discordant results between gdh and toxin A/B EIA's (n=54) were tested by 1) Rapid culture protocol; 2) conventional culture on CCFA agar followed by homebrew PCR for the toxin genes; 3) a commercial PCR (Cepheid) for toxin genes (for most of the samples). Results are shown in FIG. 1. Of the 54 discordant samples, 21 were positive by rapid culture protocol, and 4 other samples had detectable *C. difficile* by conventional culture, at very low titers (1 colony or fewer on CCFA agar). All rapid culture positive samples were confirmed to have toxin genes by homebrew PCR, and most by a commercial Cepheid PCR (17 of 18 tested; 1 indeterminate). Adding the results of rapid toxigenic culture to direct toxin A/B increased the number of positive samples from 35 to 56, and detected 56 of 60 specimens found to be positive for toxigenic *C. difficile* by any means. Sensitivity of rapid culture, when used in conjunction with direct toxin EIA was 93%, specificity 100% and yield of detection was improved by 60%.

Figure 2:
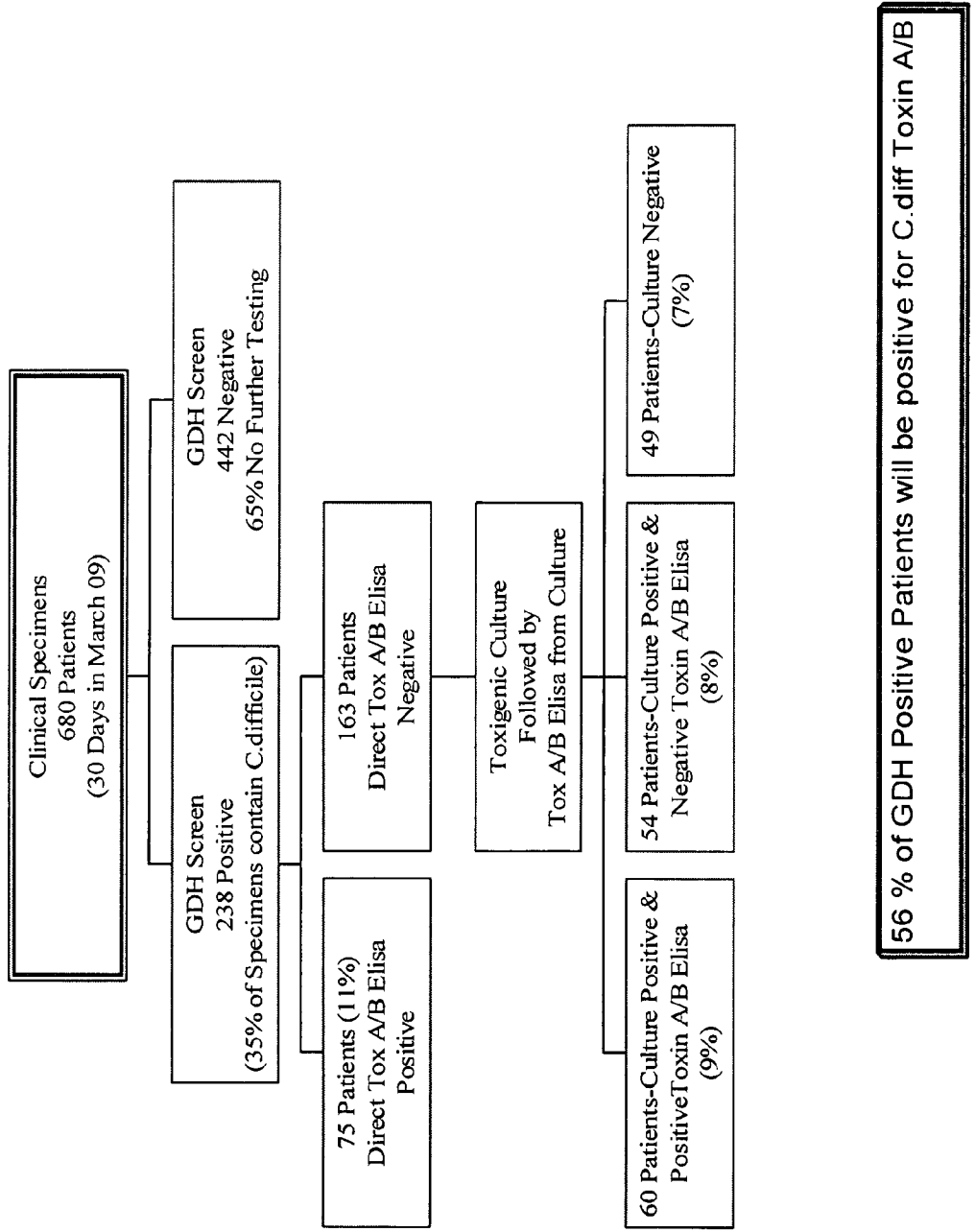
FIG. 2. Review of patient data with two-step protocol.

Based on the positive experience in the research study, this protocol was adopted by the clinical microbiology laboratory at Montefiore Medical Center, Bronx, N.Y. Results of 1 month of implementation show similar results to the pilot study (FIG. 2). Remarkably, there was an 80% increased yield of positive patient samples, from 11% detected by toxin A/B alone to 20% detected after utilization of rapid toxigenic culture protocol.

In order to assess how many samples might have been missed by restricting the culturing time to 48 hrs, further testing was conducted of 26 samples which were turbid but had negative results by toxin A/B testing after 48 hrs of growth. These broths were cultured conventionally on CCFA agar, and 3 revealed growth of toxigenic *C. difficile*. Thus, extrapolating this 11% rate of false negative turbid broths to the full month's data set, the use of rapid toxigenic culture detected 60 of 65.8 expected positive *C. difficile* cultures, for a sensitivity of 91%.

Finally, in order to speed up detection of *C. difficile*, our clinical laboratory started to use commercial PCR in lieu of toxigenic culture. By surveying results over a comparable period (Feb. 22 to Mar. 24, 2010), a similar improved yield was seen—10.6% of patients were positive for *C. difficile* infection by direct toxin A/B, with an increase to 18.1% when a commercial PCR was added.

SUMMARY

Adoption of the present invention in a clinical setting increased the identification of true *C. difficile* patients by 80%, without a great increase in cost or equipment. The material costs of this additional step of culture are $1.50 per tube, plus the cost of an additional toxin EIA assay (~$5). While rates of *C. difficile* detected increased in the hospital as a result of this intervention, the expectation is that proper identification of these patients will improve their clinical outcomes, including survival, decrease spread of the disease within the hospital due to more appropriately targeted infection control measures, and ultimately decrease *C. difficile* rates. In addition, with increased clinician confidence in a negative *C. difficile* test result, there should be decreased inappropriate overuse of "empiric" antibiotics for patients without *C. difficile*. Further, the availability of a simple, sensitive and inexpensive culture method would also be of value for environmental sampling, to ensure the adequacy of cleaning and identify environmental reservoirs of infection. Finally, the availability of clinical and/or environmental specimens allows the implementation of strain typing—to document foci of ongoing spread within the hospital—as well as antibiotic susceptibility testing to document emerging resistance, neither of which could be done previously using only EIA and/or PCR technologies for diagnosis.

REFERENCES

APIC—The Association for Professionals in Infection Control and Epidemiology, Inc. National Prevalence Study of *Clostridium difficile* in U.S. Healthcare Facilities, reported Nov. 11, 2008.

Arroyo, Luis G., Joyce Rousseau, Barbara M. Willey, Don E. Low, Henry Staempfli, Allison McGeer, and J. Scott Weese. (2005) Use of a Selective Enrichment Broth To Recover *Clostridium difficile* from Stool Swabs Stored under Different Conditions. Journal of Clinical Microbiology, October 2005, p. 5341-5343 Vol. 43, No. 10.

Buchanan, A G. (1984) Selective Enrichment Broth Culture for Detection of *Clostridium difficile* and Associated Cytotoxin. Journal of Clinical Microbiology, July 1984, p. 74-76 Vol. 20, No. 1.

Buggy, B P, K H Wilson, R Fekety. (1983) Comparison of Methods for Recovery of *Clostridium difficile* from an Environmental Surface. Journal of Clinical Microbiology, August 1983, p. 348-352 Vol. 18, No. 2.

Clabots, C R, K M Bettin, L R Peterson and D N Gerding. (1991) "Evaluation of Cycloserine-Cefoxitin-Fructose Agar and Cycloserine-Cefoxitin-Fructose Broth for Recovery of *Clostridium difficile* from Environmental Sites" Journal of Clinical Microbiology, November 1991, p. 2633-2635 Vol. 29, No. 11.

Cohen S H, Gerding D N, Johnson S, Kelly C P, Loo V G, McDonald L C, Pepin J, Wilcox M H. Clinical practice guidelines for *Clostridium difficile* infection in adults: 2010 update by the society for healthcare epidemiology of America (SHEA) and the infectious diseases society of America (IDSA). Infect Control Hosp Epidemiol. 2010 May; 31(5):431-55.

Dubberke E R, Wertheimer A I. Review of current literature on the economic burden of *Clostridium difficile* infection. Infect Control Hosp Epidemiol. 2009 January; 30(1):57-66.

Fenner, L., A. F., Widmer, G. Goy et al. 2008. Rapid and reliable diagnostic algorithm for detection of *Clostridium difficile*. J. Clin. Microbiol. 46:328-330.

George W L, Sutter V L, Citron D, Finegold S M. Selective and differential medium for isolation of *Clostridium difficile*. J Clin Microbiol. 1979 February; 9(2):214-9.

Gilligan, P. H. 2008. Is a two-step glutamate dehydrogenase antigen-cytotoxicity neutralization assay algorithm superior to the Premier toxin A and B enzyme immunoassay for laboratory detection of *Clostridium difficile*. J. Clin. Microbiol. 46:1523-1525.

Jarvis W R, Schlosser J, Jarvis A A, Chinn R Y. National point prevalence of *Clostridium difficile* in US health care facility inpatients, 2008. Am J Infect Control. 2009 May; 37(4): 263-70. Epub 2009 Mar. 10.

Johnson, L L, L V McFarland, P Dearing, V Raisys and F D Schoenknecht. (1989) Identification of *Clostridium difficile* in Stool Specimens by Culture-Enhanced Gas-Liquid Chromatography. Journal of Clinical Microbiology, October 1989, p. 2218-2221 Vol. 27, No. 10.

Kelly, C. P. and J. T. LaMont. 2008 *Clostridium difficile*-More difficult than ever. N. Eng. J. Med. 359: 1932-1940.

Kvach E J, Ferguson D, Riska P F, Landry M L. Comparison of BD GeneOhm Cdiff real-time PCR assay with a two-step algorithm and a toxin A/B enzyme-linked immunosorbent assay for diagnosis of toxigenic *Clostridium difficile* infection. J Clin Microbiol. 2010 January; 48(1):109-14. Epub 2009 Oct. 28.

Levett P N. Effect of antibiotic concentration in a selective medium on the isolation of *Clostridium difficile* from faecal specimens. *J Clin Pathol* 1985 38: 233-234

Nerandzic, M and C J. Donskey. (2009) "Effective and Reduced-Cost Modified Selective Medium for Isolation of *Clostridium difficile*" Journal of Clinical Microbiology, February 2009, p. 397-400.

Ohio Department of Health report 2007: www.odh.ohio.gov/ASSETS/5EA5D246A2AB478686F8C8D6CCAAFEBC/C%20diff%020Final%20Report03012007.pdf Planche, T., A. Aghaizu, R. Holliman, et al. 2008. Diagnosis of *Clostridium difficile* infection by toxin detection kits: a systematic review. theLancet.com/Infection Nov. 1, 2008: 1-8.

Reller, M. E., C. A. Lema, T. M. Perl et al. 2007. Yield of Stool culture with isolate toxin testing versus a two-step algorithm including stool toxin testing for detection of toxigenic *Clostridium difficile*. J. Clin. Microbiol 45:3601-36046.

Robertson, M. 1916. Notes upon certain anaerobes isolated from wounds. J. Pathol. Bacteriol. 20:327-349.

She R C, Durrant R J, Petti C A. Evaluation of enzyme immunoassays to detect *Clostridium difficile* toxin from anaerobic stool culture. Am J Clin Pathol. 2009 January; 131(1):81-4.

Sloan L M, Duresko B J, Gustafson D R, Rosenblatt J E. Comparison of real-time PCR for detection of the tcdC gene with four toxin immunoassays and culture in diagnosis of *Clostridium difficile* infection. J Clin Microbiol. 2008 June; 46(6):1996-2001. Epub 2008 Apr. 23.

Stamper, P. D., R. Alcabasa, D. Aird, et al. 2009. Comparison of a commercial Real-Time PCR assay for tcdB detection to cell culture cytotoxicity assay and toxigenic culture for detection of toxin-producing *Clostridium difficile* in Clinical samples. J. Clin Microbiol. 47:373-378.

Ticehurst, J. R., D. Z. Aird, L. M. Dam, et al. 2006. Effective detection of toxigenic *Clostridium difficile* by a two-step algorithm including tests for antigen and cytotoxin. J. Clin. Microbiol. 44:1145-1149.

U.S. Pat. No. 4,530,833, Wilkins et al., Jul. 23, 1985, Toxins and antibodies of *C. difficile*.

U.S. Pat. No. 4,533,630, Wilkins et al., issued Aug. 6, 1985, Toxins and antibodies of *C. difficile.*

U.S. Pat. No. 4,863,852, Wilkins et al., issued Sep. 5, 1989, Method of detecting, isolating and purifying *clostridium difficile* toxin A and its receptors.

U.S. Pat. No. 4,879,218, Wilkins et al., Nov. 7, 1989, Antibody for *C. difficile.*

U.S. Pat. No. 5,098,826, Wilkins et al., issued Mar. 24, 1992, Detection, isolation and purification of *Clostridium difficile* toxin A with toxin receptors.

U.S. Pat. No. 5,965,375, Valkirs, issued Oct. 12, 1999, Diagnostic tests and kits for *Clostridium difficile.*

U.S. Pat. No. 6,503,722, Valkirs issued Jan. 7, 2003, Diagnostic tests and kits for *Clostridium difficile.*

U.S. Pat. No. 7,179,611, Deutsch, issued Feb. 20, 2007, Mono-specific polyclonal antibodies and methods for detecting *Clostridium difficile* Toxin A.

What is claimed is:

1. A culture medium for *Clostridium difficile* comprising Cooked Meat Medium with glucose;

yeast extract in a concentration of 2 to 10 g/L;

taurocholate in a concentration of 0.05 to 0.1%;

cycloserine in a concentration of 200 to 400 μg/mL; and cefoxitin in a concentration of 8 to 32 μg/mL.

2. The culture medium of claim 1, wherein taurocholate is present in a concentration of 1.0 mg/mL.

3. The culture medium of claim 1, wherein cycloserine is present in a concentration of 250 μg/ml.

4. The culture medium of claim 1, wherein cefoxitin is present in a concentration of 16 μg/mL.

5. The culture medium of claim 1, wherein the yeast extract is present in a concentration of 5 gm/liter.

6. The culture medium of claim 1, comprising Hemin and/or Vitamin K.

7. A method for diagnosing the presence of toxigenic *Clostridium difficile* in a sample comprising:

a) treating the sample with alcohol;

b) incubating the alcohol-treated sample in a medium comprising Cooked Meat Medium width glucose; yeast extract; taurocholate; cycloserine; and cefoxitin for 24 to 72 hours;

c) testing the sample after the 24 to 72 hour incubation of step b) for the presence of *Clostridium difficile* toxin A and/or toxin B;

wherein the presence of *Clostridium difficile* toxin A and/or toxin B indicates the presence of *Clostridium difficile* in the sample.

8. The method of claim 7, wherein the sample is a stool sample or an environmental sample.

9. The method of claim 7, wherein the alcohol is methanol, ethanol or propanol.

10. The method of claim 7, wherein the ratio of sample to alcohol in step a) is 50-500 μl of sample to 1 ml of alcohol.

11. The method of claim 7, wherein the ratio of sample to alcohol in step a) is 200 μl of sample to 1 ml of alcohol.

12. The method of claim 7, wherein the alcohol is ethanol.

13. The method of claim 12, wherein the final concentration of ethanol after addition of the sample in step a) is 50-90% ethanol.

14. The method of claim 7, wherein for step a), the duration of treatment ranges from 15 minutes to 1 month.

15. The method of claim 7, wherein for step a), the duration of treatment is 30 minutes.

16. The method of claim 7, wherein the ratio of alcohol treated sample to Cooked Meat Medium in step b) is 50-250 μl of alcohol treated sample to 10 ml of Cooked Meat Medium.

17. The method of claim 7, wherein step b) is carried out at a temperature of 37° C.

18. The method of claim 7, wherein taurocholate is present in a concentration of 0.05-0.1%.

19. The method of claim 7, wherein taurocholate is present in a concentration of 1.0 mg/mL.

20. The method of claim 7, wherein cycloserine is present in a concentration of 200 to 400 μg/ml.

21. The method of claim 7, wherein cycloserine is present in a concentration of 250 μg/ml.

22. The method of claim 7, wherein cefoxitin is present in a concentration of 8 to 32 μg/ml.

23. The method of claim 7, wherein cefoxitin is present in a concentration of 16 μg/mL.

24. The method of claim 7, wherein the yeast extract is present in a concentration of 2 to 10 gm/liter.

25. The method of claim 7, wherein the yeast extract is present in a concentration of 5 gm/liter.

26. The method of claim 7, wherein the medium in step b) comprises Hemin and/or Vitamin K.

27. The method of claim 7, wherein step b) is carried out for 48 hours.

28. The method of claim 7, wherein the presence of *C. difficile* toxin A and/or toxin B is tested using an EIA assay.

29. The method of claim 7 wherein the incubating of step b) can be performed in either an aerobic or anaerobic incubator.

30. A kit for diagnosing the presence of toxigenic *Clostridium difficile* comprising the culture medium of claim 1.

31. The kit of claim 30, wherein the kit comprises alcohol.

32. The kit of claim 31, comprising ethanol.

33. The kit of claim 30, wherein the kit comprises instructions for carrying out a method for diagnosing the presence of toxigenic *Clostridium difficile* in a sample.

* * * * *